(12) United States Patent
Maeda et al.

(10) Patent No.: US 6,425,418 B1
(45) Date of Patent: Jul. 30, 2002

(54) FLEXIBLE TUBE AND MANUFACTURING METHOD FOR THE SAME

(75) Inventors: Shigeo Maeda, Itami; Masayoshi Esashi; Yoichi Haga, both of Sendai, all of (JP)

(73) Assignee: Mitsubishi Cable Industries, Ltd., Amagasaki (JP)

( * ) Notice: Subject to any disclaimer, the term of this patent is extended or adjusted under 35 U.S.C. 154(b) by 17 days.

(21) Appl. No.: 09/635,535

(22) Filed: Aug. 9, 2000

(30) Foreign Application Priority Data

Oct. 27, 1999 (JP) .......................... 11-305513
Nov. 8, 1999 (JP) .......................... 11-316972

(51) Int. Cl.$^7$ .............................. F16L 11/00; A61F 2/06
(52) U.S. Cl. ...................... 138/133; 138/134; 138/144; 138/145
(58) Field of Search .................... 138/129, 131–133, 138/134, 146, 144, 145; 604/525

(56) References Cited

U.S. PATENT DOCUMENTS

| 3,083,736 A | * | 4/1963 | Roberts et al. ............ 138/122 |
| 5,795,318 A | * | 8/1998 | Wang et al. .................. 604/8 |
| 5,961,547 A | * | 10/1999 | Razavi ...................... 623/1.22 |
| 6,296,615 B1 | * | 10/2001 | Brockway et al. .......... 600/485 |

OTHER PUBLICATIONS

US 2001/016728 Kelley US patent application publication Aug. 23, 2001.*

* cited by examiner

Primary Examiner—Patrick Brinson
(74) Attorney, Agent, or Firm—Armstrong, Westerman & Hattori, LLP

(57) ABSTRACT

A flexible tube having a construction in which a coil of metal is coated with a film of resin. The flexible tube is manufactured by that resin is vapor-deposited on a peripheral face of a thermocontraction tube. a metal wire is wound on the tube as to be coiled, resin is vapor-deposited on the coil, and the thermocontraction tube is contracted by heating and drawn out.

5 Claims, 8 Drawing Sheets

FLEXIBLE TUBE AND MANUFACTURING METHOD FOR THE SAME

BACKGROUND OF THE INVENTION

1. Field of the Invention

This invention relates to a flexible tube and its manufacturing method, especially, a flexible tube for construction of endoscopes, catheters, guide wires, and artificial blood vessels, and manufacturing method for the same.

2. Description of the Related Art

In these days, apparatuses such as endoscopes, catheters, guide wires are used frequently to be inserted to blood vessels and intestines for examination and operation of human bodies. Each of these apparatuses has a distal portion which bends corresponding to configuration of the blood vessels and the intestines on its end portion or entire body for smooth insertion to the blood vessels and the intestines. Generally, the distal portion is composed of a flexible tube.

The apparatuses such as endoscopes, catheters, and guide wires contact inner portions of the blood vessels and the intestines. For this reason, the flexible tube of which these apparatuses are composed is required to bend smoothly (to be excellent in flexibility). And, wall of the tube is required to be thin to make the outer diameter of the apparatus as small as possible. To fulfill these requirements, conventionally, a rubber tube of thin wall formed by extruding method, a braided metal wire tube composed of a synthetic resin tube covered with metal wires etc. are used as the flexible tube.

And, Japanese life style has been westernized recently, and diseases related to arteriosclerosis have been increasing. Therefore, the demand for artificial blood vessel is becoming stronger year after year. Generally, material for artificial blood vessel is required to have physical and chemical stability in vivo, safety, appropriate anti-thrombotic character, anti-fatigue strength, elastic extensionality similar to that of living organism. And, after the artificial blood vessel is embedded in living organism, a tissue similar to vascular wall is generated on an inner face of the artificial blood vessel. Therefore, it is preferable that the material for artificial blood vessel is effective for forming endoderm cells and regeneration of vascular tissue.

Currently, polyester artificial blood vessels and Teflon artificial blood vessels are applied clinically. The polyester artificial blood vessel is made by that synthetic fibers obtained by melt spinning of polyethylene terephthalate are braided in a tube. And, the Teflon artificial blood vessel is made by that a tube made of polytetrafluoret hylene is extended under certain conditions to fibrilate (microfiberize) the wall construction of the tube.

However, when applied to the flexible tube used for the distal portion mentioned above, although the rubber tube is excellent in flexibility, buckling and twist (kink) are easily generated, and the tube is breakable when it is bent. On the contrary, the above-mentioned braided metal wire tube has advantages that the buckling and the twist are hardly generated and the tube is not breakable, and disadvantages that flexibility is not sufficient and the tube is difficult to be made small in diameter and thin in wall thickness.

On the other hand, a bellows tube is known to solve these disadvantages. The bellows tube has a construction in which a metal coil is embedded in a tube wall formed with resin, and the disadvantages above is to be solved by the construction. Normally, the bellows tube is made by a dipping method in which a metal coil is dipped in melted resin and drawn out of the resin to be a tube, and a taping method in which resin tapes are wound around a coil or disposed in a longitudinal direction on the coil.

The coil is exposed inside the tube in the tube made by the taping method.

However, in the dipping method described above, wall thickness of the bellows tube is difficult to be uniform and thin. Further, in the taping method described above, it is difficult to wind or dispose the tape when the outer diameter of the coil is small. Therefore, it is very difficult to make a bellows tube having outer diameter less than several millimeters conventionally.

And, in the artificial blood vessel described above, the polyester artificial blood vessel and the Teflon artificial blood vessel have problems that crimp (kinking) is generated when the blood vessel is bent and the buckling tends to be generated. These problems are expected to become more serious when the artificial blood vessels will be used as substitute for small blood vessels excluding aorta in the near future.

It is therefore an object of the present invention to provide a flexible tube especially used for endoscopes and artificial blood vessels having excellent mechanical characteristics restricting the crimp phenomenon and buckling in bending, small diameter, and thin tube wall, and a manufacturing method for the flexible tube.

BRIEF DESCRIPTION OF THE DRAWINGS

The present invention will be described with reference to the accompanying drawings, in which.

DESCRIPTION OF THE PREFERRED EMBODIMENTS

Preferred embodiments of the present invention will now be described with reference to the accompanying drawings.

Figure 1:
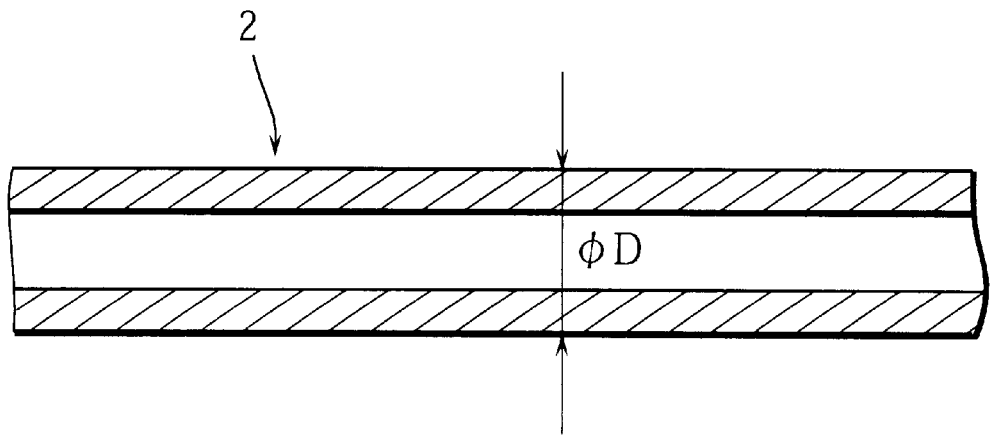
FIG. 1 is an enlarged cross-sectional view showing a first process of the manufacturing method relating to a first embodiment of the present invention.

FIG. 1 shows a first preferred embodiment of a flexible tube and manufacturing method for the same relating to the present invention. The first preferred embodiment of present invention is, especially, restricted to use for an endoscope.

FIG. 1 through FIG. 5 are enlarged cross-sectional views to explain processes of a manufacturing method of the flexible tube 1 of the first preferred embodiment of the present invention.

First, release agent is painted on a peripheral face of a thermocontraction tube 2 as a mandrel made of synthetic resin which is contracted by heating as shown in FIG. 1. For example, outer diameter D of the (thermocontraction) tube 2 is set to be 2 to 5 mm.

Figure 2:
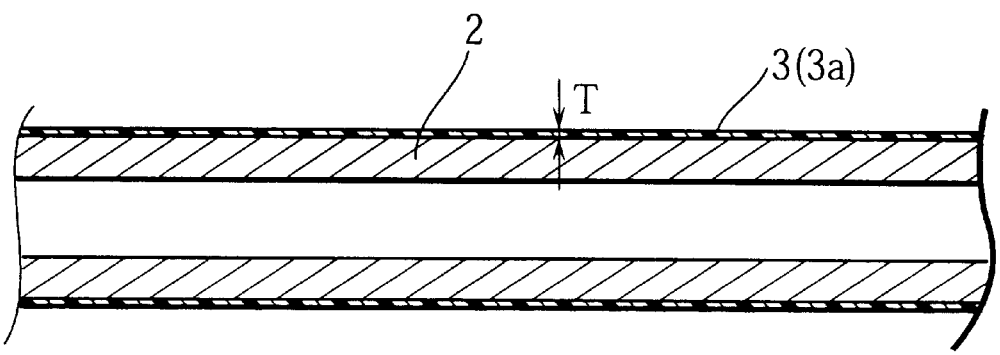
FIG. 2 is an enlarged cross-sectional view showing a second process of the manufacturing method relating to the present invention.

Next, as shown in FIG. 2, (vaporized) resin 3 is vapor-deposited on the peripheral face of the (thermocontraction) tube 2 painted with the release agent to form a first (vaporized) resin layer 3a of which thickness T is 1 $\mu$m to 25 $\mu$m (preferably 2 $\mu$m to 10 $\mu$m).

As the (vaporized) resin 3, for example, poly-para-xylylene, which is sold under a tradename "parylene" of ThreeBond Co., Ltd., can be used.

If the thickness of the first resin layer 3a is less than the minimum value, strength is insufficient. On the contrary, if the thickness is more than the maximum value, the tube can not correspond to requirement as a flexible tube for an endoscope that wall thickness should be as small as possible.

Figure 3:
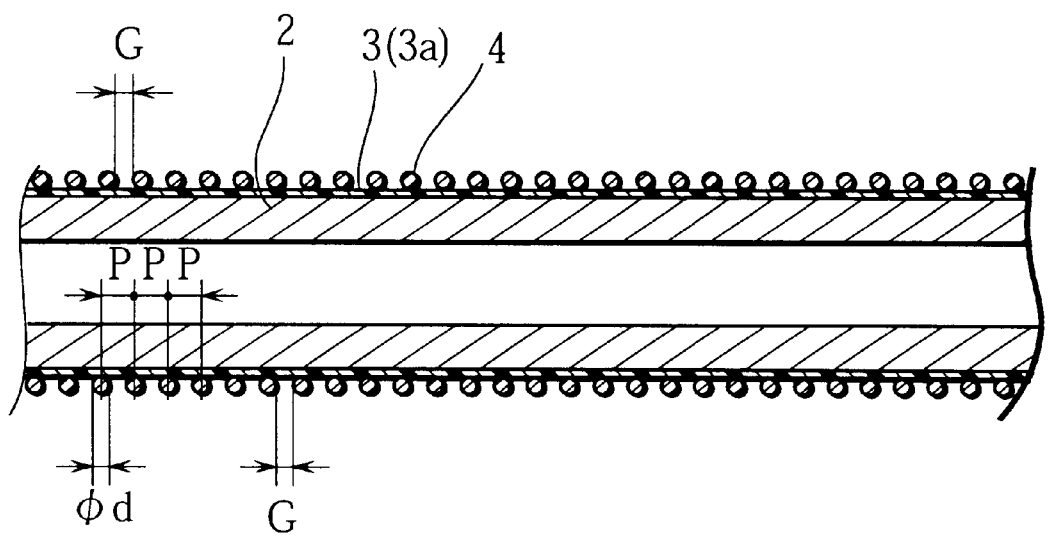
FIG. 3 is an enlarged cross-sectional view showing a third process of the manufacturing method relating to the present invention.

Then, as shown in FIG. 3, a metal wire is wound to the tube as to form a gap G to form a coil 4. For example, soft stainless steel wire of which diameter d is 0.1 mm is wound with a pitch P of 0.2 mm. The coil 4 is wound thereby.

Figure 4:
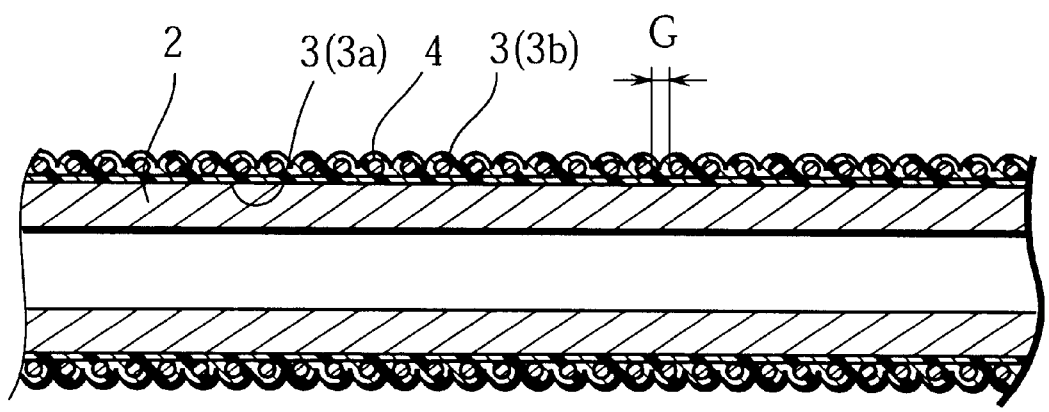
FIG. 4 is an enlarged cross-sectional view showing a fourth process of the manufacturing method relating to the present invention.

Next, as shown in FIG. 4, the (vaporized) resin 3 is vapor-deposited on the tube to form a second (vaporized) resin layer 3b. The material and thickness of the second resin layer 3b are similar to (same as) that of the first resin layer 3a described above. The second resin layer 3b fits to the first resin layer 3a unitedly because the coil 4 has the gap G.

After the (thermocontraction) tube 2 is covered with the first resin layer 3a, the coil 4, and the second resin layer 3b successively, the whole is heated to contract the (thermocontraction) tube 2 (as the mandrel). And the contracted tube 2 can be drawn out as shown with two-dot broken lines and an arrow A in FIG. 5 thereby.

Figure 5:
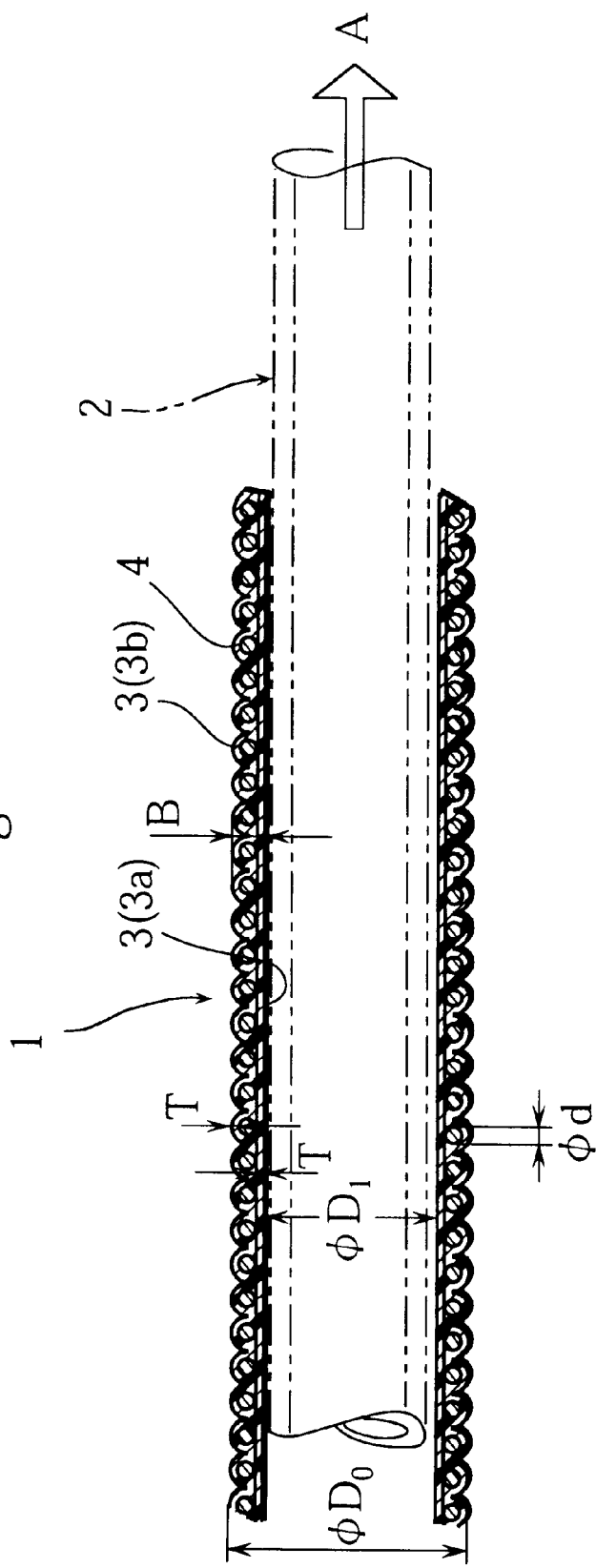
FIG. 5 is an enlarged cross-sectional view showing a fifth process of the manufacturing method and a flexible tube relating to the present invention.

By the manufacturing method described above, the flexible tube 1 as shown with a continuous line in FIG. 5 having an extremely small wall thickness B is obtained.

And, the flexible tube 1 for an endoscope has an inner diameter $D_1$ of equal to or less than 5 mm and a construction in which the coil 4 is coated with the first resin layer 3a from inside and the second resin layer 3b from outside by vapor deposition and formed into a small tube.

For example, when the outer diameter D of the tube 2 is 3 mm, the thickness T of the first resin layer 3a and the second resin layer 3b is 5 $\mu$m, and the diameter d of the coil 4 is 0.1 mm, in FIG. 5, the outer diameter $D_0$ of the flexible tube 1 is (3+0.005×4+0.1×2)mm=3.22 mm, and the flexible tube having the extremely thin wall thickness B (which is impossible to achieve with the conventional bellows tube) and sufficiently small outer diameter Do can be made.

The flexible tube 1 having these dimensions was actually made with poly-para-xylylene (parylene) as the first and second resin layers 3a and 3b and soft stainless steel wire as the coil 4. With the flexible tube 1, extension amount is 1.5 to 2 times larger than that of conventional flexible tubes, minimum bending radius of about 5 mm is sufficiently small, and strength against twist is also high.

Figure 6:
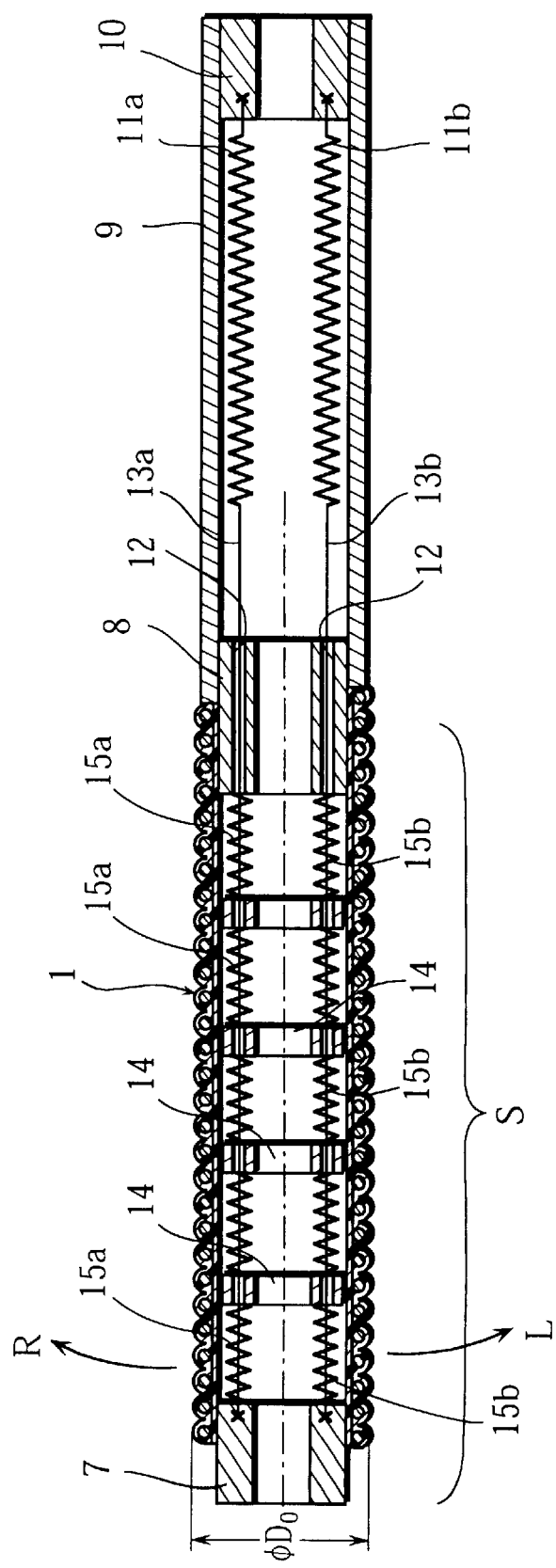
FIG. 6 is an enlarged cross-sectional view showing an applied example.

FIG. 6 shows a schematic view of an applied example in which the flexible tube 1 is applied to a distal portion S of an endoscope.

That is to say, a forth end holder 7 and a base end side holder 8 of the distal portion S are connected to and united with the flexible tube 1 relating to the present invention. Further, a metal pipe 9 is extended for a predetermined length to the base end through the base end side holder 8, and a base member 10 is fixed to the base end side of the metal pipe 9. And, two tension coils 11a and 11b made of shape memory alloy are inserted to the metal pipe 9, and drawing wires 13a and 13b connected to the tension coil 11a and 11b respectively are inserted to insertion holes 12 of the base end side holder 8 and connected to the forth end holder 7.

Further, multilumen sectional bodies 14 are disposed inside the flexible tube 1 with a predetermined pitch in an axis direction, the drawing wires 13a and 13b are inserted to small holes in the multilumen sectional body 14, and a compression coil 15a and a compression coil 15b are disposed respectively (as shown in FIG. 6) between the neighboring multilumen sectional bodies 14, between the forth end holder 7 and the multilumen sectional body 14 on the forth end side, and between the base end side holder 8 and the multilumen sectional body 14 on the base end side.

As described above, the compression coils 15a and 15b are disposed in the distal portion S, and balanced with the tension coil 11a and 11b (in the pipe 9 on the base end side) through the inside drawing wires 13a and 13b.

Therefore, when the tension coil lha is heated by electricity, the distal portion S swings in the direction of an arrow R, and when the compression coils 15a are heated by electricity, the distal portion S returns to the initial configuration. On the contrary, when the tension coil lib is heated by electricity, the distal portion S swings in the direction of an arrow L, and when the compression coils 15b are heated by electricity, the distal portion S returns to the initial configuration.

And, in case that the tension coils 11a and 11b are simultaneously heated by electricity, the distal portion S contracts in the axis direction instead of swinging in the both of the directions of the arrows R and L, and (bending) rigidity of the distal portion S can be improved thereby. The flexible tube 1 relating to the present invention can also correspond to this movement of contraction in the axis direction. The flexible tube 1 of the present invention can be applied to various distal portions other than the distal portion S shown in FIG. 6. And, driving mechanism (such as an actuator) for the swing movement is not restricted.

Figure 7A:
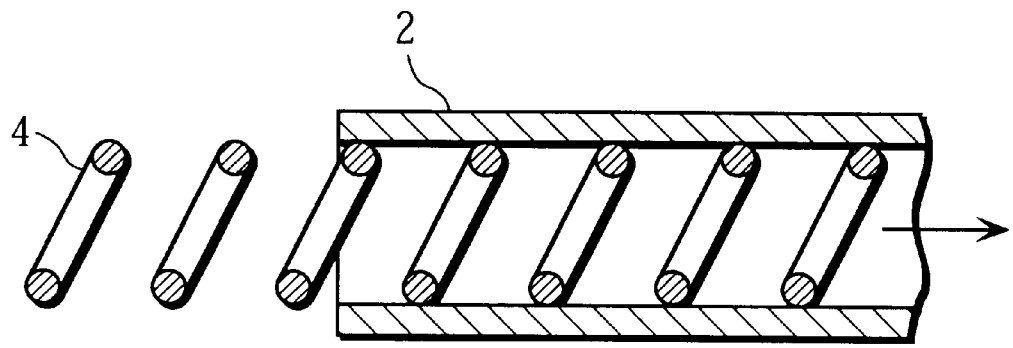
FIG. 7A is an enlarged cross-sectional view showing a first process of the manufacturing method relating to a second embodiment of the present invention.
Figure 7B:
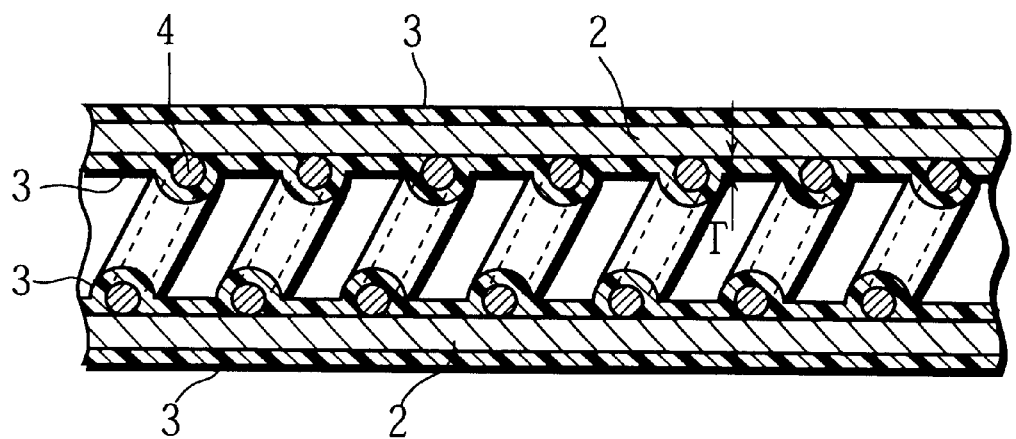
FIG. 7B is an enlarged cross-sectional view showing a second process of the manufacturing method relating to the present invention.
Figure 7C:
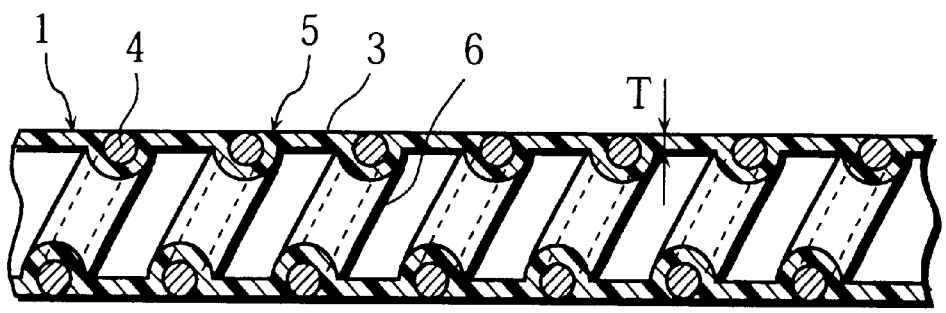
FIG. 7C is an enlarged cross-sectional view showing a third process of the manufacturing method and a flexible tube relating to the present invention.
Figure 8:
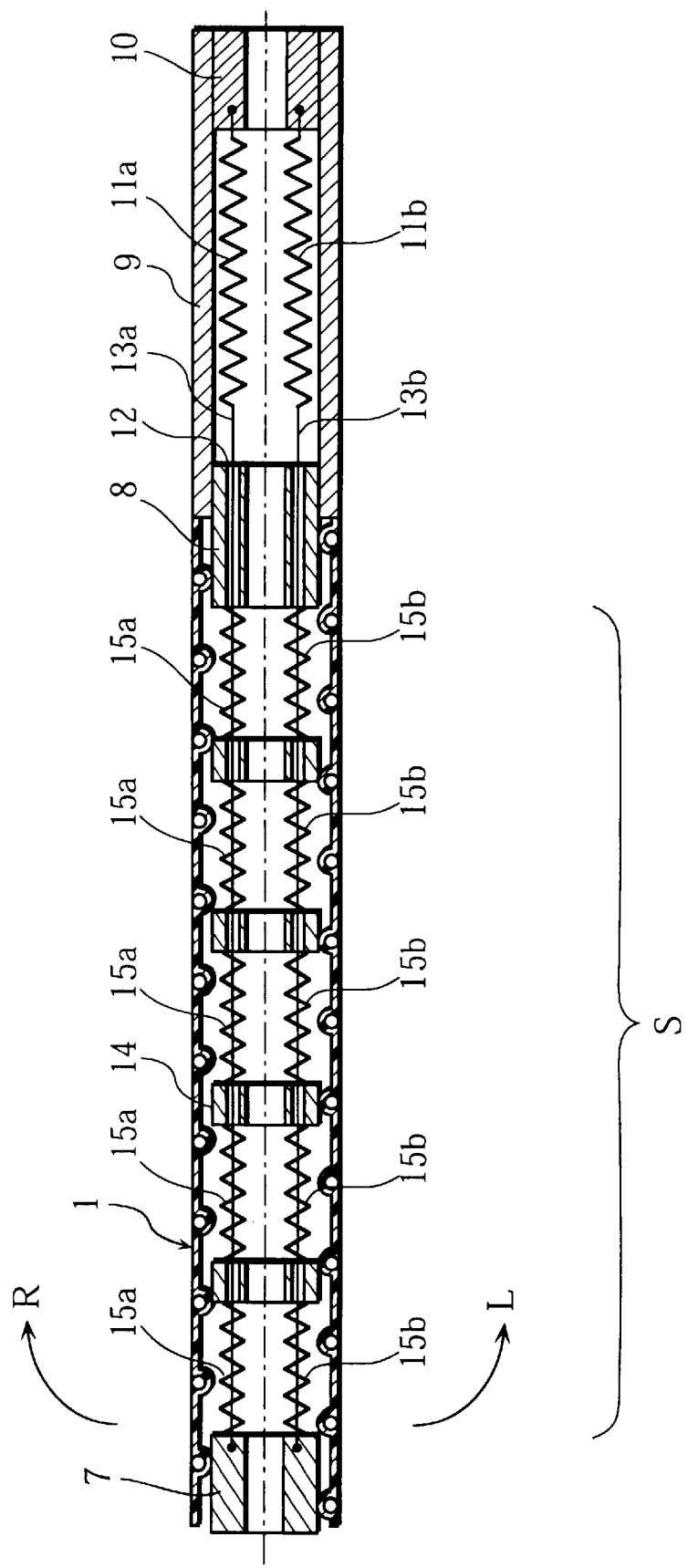
FIG. 8 is an enlarged cross-sectional view showing an example of a distal portion of an endoscope constructed with the flexible tube relating to the present invention.

Next, FIG. 7 and FIG. 8 show a second embodiment of the flexible tube and the manufacturing method relating to the present invention. The second embodiment of the present invention is, especially, restricted to endoscopes, catheters, and guide wires. As clearly shown in comparison with the first embodiment described above, following construction is different. Explanation of the same marks is omitted because they are constructed similar to that of the first embodiment.

That is to say, FIG. 7A through FIG. 7C are enlarged cross-sectional views to explain processes of the manufacturing method of the flexible tube 1 of the second embodiment of the present invention. First, a process in which the coil 4 is covered with the tube 2 is conducted as shown in FIG. 7A. Although the inner diameter of the tube 2 and the outer diameter of the coil 4 are set to be same in FIG. 7A, they are not restricted to this condition in the present invention. In the present invention, metal such as stainless steel, polymer such as polyimide are preferably used for forming the coil 4. In the present invention, the coil 4 may extend to the entire flexible tube, or a part of the flexible tube. In the present invention, plural coils 4 can be used for a piece of tube 2. In this case, a flexible tube having plural parts where a coil is embedded in the wall of the tube can be obtained.

Specifications of the coil 4 such as outer diameter, diameter of the wire, pitch of the coil, number of winding are properly set corresponding to purposes of the flexible tube such as for an endoscope, a catheter, and a guide wire, and size of parts inside these apparatuses.

For example, when the tube is used for an endoscope, it is preferable to set the outer diameter 1 mm to 10 mm, the length 1 m to 1.5 m (when partially used, 5 mm to 30 mm, especially 10 mm to 20 mm), the diameter of the wire 0.01 mm to 0.2 mm, and the pitch of the coil 0.02 mm to 1 mm. When the tube is used for a catheter, it is preferable to set the outer diameter 0.5 mm to 3 mm, the length 1 m to 1.5 m (when partially used, 5 mm to 30 mm, especially 10mm to 20 mm), the diameter of the wire 0. 01 mm to 0.2 mm, and the pitch of the coil 0.02 mm to 1 mm. When the tube is used for a guide wire, it is preferable to set the outer diameter 0.3 mm to 0.5 mm, the length 1 m to 1.5 m (when partially used, 5 mm to 30 mm, especially 10 mm to 20 mm), the diameter of the wire 0.005 mm to 0.1 mm, and the pitch of the coil 0.01 mm to 0.2 mm.

As the tube 2, while a tube formed with various rubber materials, a tube formed with resin, etc. can be used, a silicone tube is preferably used because it is excellent in expandability and flexibility, and easily removed by wet etching. The inner diameter and length of the tube 2 may be appropriately set to respond to required outer diameter and length of the flexible tube, and outer diameter and length of the coil 4. However, wall thickness of the tube 2 is preferably set to be about 0.01 mm to 0.5 mm, more preferably about 0.1 mm to 0.15 mm because it is necessary to shorten the time for removing the tube. Difference between the inner diameter of the tube 2 and the outer diameter of the coil 4 is set to be 0 $\mu$m to 100 $\mu$m, preferably 0 $\mu$m to 20 $\mu$m for making the wall thickness of the obtained flexible tube thin.

Next, as shown in FIG. 7B, a process in which at least the inner side of the tube 2 and the coil 4 are coated with resin 3 is conducted. As the coating method of the present invention, deposition method such as vacuum deposition method and fluidized dip coating method, etc. can be used. Among these methods, vacuum deposition method is preferably used because uniform thin film can be formed even on an intricate configuration and the thickness of the thin film can be accurately controlled. In FIG. 7B, a coating layer of the resin 3 is also formed on the outside of the tube 2 because the coating is conducted with the vacuum deposition method. The present invention is not restricted to this example.

The coating is preferably conducted as to make thickness T of the resin 3 being 1 $\mu$m to 25 $\mu$m, more preferably 2 $\mu$m to 10 $\mu$m. If the thickness is less than 1 $\mu$m, the flexible tube does not have sufficient strength. If the thickness is more than 25 $\mu$m, the outer diameter of the flexible tube have to be large to keep storing space for an actuator, etc., and flexibility of the flexible tube is spoiled. As concrete examples of the coated resin 3, poly-para-xylylene, polyimide (formed by polymerization with vapor-deposition), polyurethan (formed by dipcoating), etc. can be used. Among them, poly-para-xylylene is preferably used because heating is not necessary, the coating can be conducted under room temperature, and resistant to most solvents.

Finally, the flexible tube 1 of the present invention is obtained as shown in FIG. 7C after a removing process of the tube 2 is conducted. The flexible tube 1 is composed of a wall 5, and the wall 5 is formed with the resin 3 coated as shown in FIG. 7B. The flexible tube 1 has a construction in which the coil 4 is embedded in the wall 5 formed with the resin 3. In the flexible tube 1, although the outside of the wall 5 is formed flat, a spiral convex portion 6 is formed inside the wall 5 along the coil 4.

As a removing method of the tube 2, polishing, etching such as wet etching, dry etching by plasma, and a combination of these methods can be used. Among these methods, etching is preferable because only the tube 2 can be removed completely. However, in the example shown in FIG. 7C, the removal is conducted with a combination of polishing and etching to remove the etching-resistant resin 3 on the outside of the tube 2.

And, although surface of the coil 4 touching the inner face of the tube 2 is exposed from the coating layer of the resin 3 in the flexible tube 1 in FIG. 7, the present invention is not restricted to this embodiment. In the present invention, the flexible tube 1 may not have exposed parts of the coil 4 depending on use of the flexible tube. For example, the flexible tube 1 without exposed parts of the coil 4 can be made with the tube 2 having an inner diameter larger than the outer diameter of the coil 4, re-deposition of the resin, etc. And, the exposed part may be coated by afterprocess. The outer diameter of the flexible tube 1 (the wall 5) is preferably the outer diameter of the coil 4+(0 $\mu$m to 50 $\mu$m).

As described above, according to the manufacturing method of the present invention, a flexible tube having an outer diameter equal to or approximately same as the outer diameter of the coil can be made. That is to say, even a tube of small diameter, having an outer diameter less than several millimeters which can not be made with the conventional bellows tube, can be easily made using a coil adjusted to the outer diameter. For example, in the example shown in FIG. 7, a flexible tube having an outer diameter of 1.1 mm can be easily made with a coil having an inner diameter of 1 mm and a diameter of wire of 0.05 mm. And, sufficiently thin wall thickness can be achieved by making the thickness of the coated resin because the flexible tube has a construction in which the coil is embedded in the wall. Further, uniformity of the wall thickness can be easily achieved.

FIG. 8 shows an example of a distal portion composed of the flexible tube of the present invention shown in a cross section. Explanation of construction, working, and effect of the distal portion are omitted because they are similar to that of the first embodiment (in FIG. 6) described above.

Next, FIG. 9 shows a third embodiment of the flexible tube and the manufacturing method relating to the present invention. The third embodiment of the present invention is, especially, restricted to artificial blood vessels. As clearly shown in comparison with the first embodiment and the second embodiment described above, following construction is different. Explanation of the same marks is omitted because they are constructed similar to that of the first embodiment and the second embodiment.

Figure 9A:
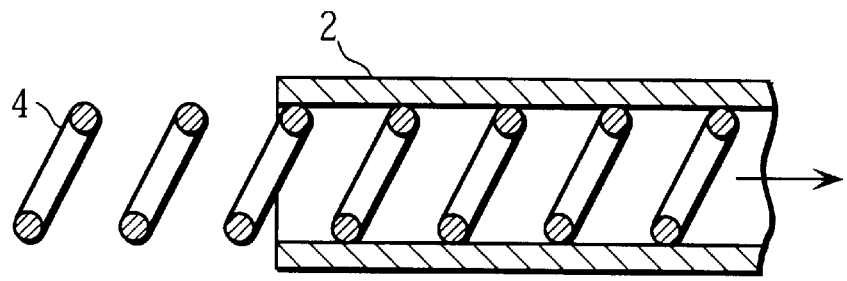
FIG. 9A is an enlarged cross-sectional view showing a first process of the manufacturing method relating to a third embodiment of the present invention.

That is to say, FIG. 9A through FIG. 9E are enlarged cross-sectional views to explain processes of the manufacturing method of the flexible tube 1 of the second embodiment of the present invention. First, a process in which the coil 4 is covered with the tube 2 is conducted as shown in FIG. 9A. The inner diameter of the tube 2 and the outer diameter of the coil 4 are set to be same in FIG. 9A. However, they are not restricted to this condition in the present invention. In the present invention, metal such as stainless steel, or polymer such as polyimide is preferably used for forming the coil 4. Specifications of the coil 4 such as outer diameter, length, diameter of the wire, pitch of the coil are properly set corresponding to purposes of the artificial blood vessel to be made.

For example, when the tube is used for an aorta, it is preferable to set the outer diameter 20 mm to 30 mm, the length 0.2 m to 0.7 m, the diameter of the wire 0.1 mm to 2 mm, and the pitch of the coil 0.2 mm to 4 mm. When the tube is used for a coronary artery, it is preferable to set the outer diameter 5 mm to 8 mm, the length 20 m to 60 m, the diameter of the wire 0.05 mm to 0.2 mm, and the pitch of the coil 0.1 mm to 0.4 mm. When the tube is used for an arteriole, it is preferable to set the outer diameter 0.1 mm to 3 mm, the length 10 m to 200 m, the diameter of the wire 0.01 mm to 0.1 mm, and the pitch of the coil 0.02 mm to 0.2 mm.

And, as the tube 2, a silicone tube is preferably used because it is excellent in expandability and flexibility, and easily removed by wet etching. The inner diameter and length of the tube 2 may be appropriately set to correspond to required outer diameter and length of the flexible tube, and outer diameter and length of the coil 4. However, wall thickness of the tube 2 is preferably set to be about 0.01 mm to 0.5 mm, more preferably about 0.1 mm to 0.15 mm because it is necessary to shorten the time for removing the tube. Difference between the inner diameter of the tube 2 and the outer diameter of the coil 4 is set to be 0 μm to 500 μm, preferably 0 μm to 50 μm for making the wall thickness of the obtained flexible tube (artificial blood vessel) thin.

Figure 9B:
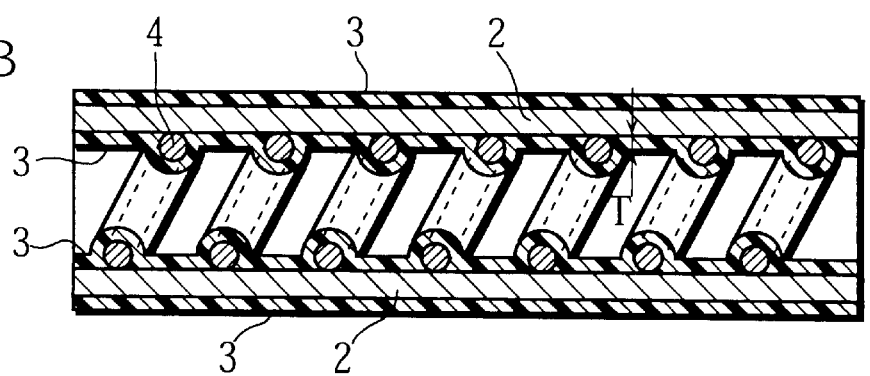
FIG. 9B is an enlarged cross-sectional view showing a second process of the manufacturing method relating to the present invention.

Next, as shown in FIG. 9B, a process in which at least the inner side of the tube 2 and the coil 4 are coated with resin 3 is conducted. In FIG. 9B, a coating layer of the resin 3 is also formed on the outside of the tube 2 because the coating is conducted with the vacuum deposition method. The present invention is not restricted to this example.

The coating is preferably conducted as to make thickness T of the resin 3 being 1 μm to 25 μm, more preferably 2 μm to 10 μm. If the thickness is less than 1 μm, the flexible tube (artificial blood vessel) does not have sufficient strength. If the thickness is more than 25 μm, flexibility of the flexible tube (artificial blood vessel) is spoiled. As a concrete example of the coated resin 3, poly-para-xylylene is preferably used.

Figure 9C:
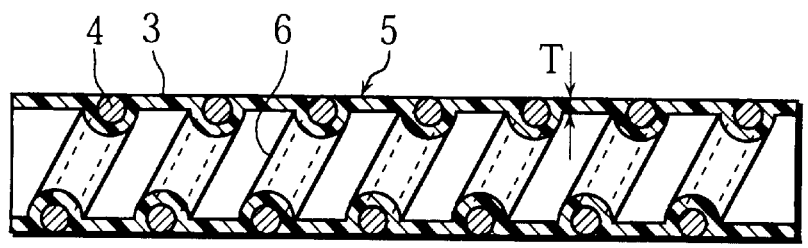
FIG. 9C is an enlarged cross-sectional view showing a third process of the manufacturing method relating to the present invention.

Next, as shown in FIG. 9C, a removing process of the tube 2 is conducted to form a wall 5. The wall 5 is formed with the resin 3 coated as shown in FIG. 9B. The coil 4 is embedded in the wall 5, the outside of the wall 5 is formed flat, and a spiral convex portion 6 is formed inside the wall 5 along the coil 4.

And, surface of the coil 4 touching the inner face of the tube 2 is exposed from the coating layer of the resin 3 in the flexible tube 1 in FIG. 9C. In this case, the outer diameter of the wall 5 is equal to the outer diameter of the coil 4. However, in the present invention, the coil may not be exposed with the tube 2 having an inner diameter larger than the outer diameter of the coil 4, re-deposition of the resin, etc. The outer diameter of the wall 5 is preferably the outer diameter of the coil+(0 μm to 50 μm), and more preferably the outer diameter of the coil+(1 μm to 10 μm).

As a removing method of the tube 2, wet etching is preferable because only the tube 2 can be removed completely. However, in the example shown in FIG. 9C, the removal is conducted with a combination of polishing and etching to remove the etching-resistant resin 3 on the outside of the tube 2.

Figure 9D:
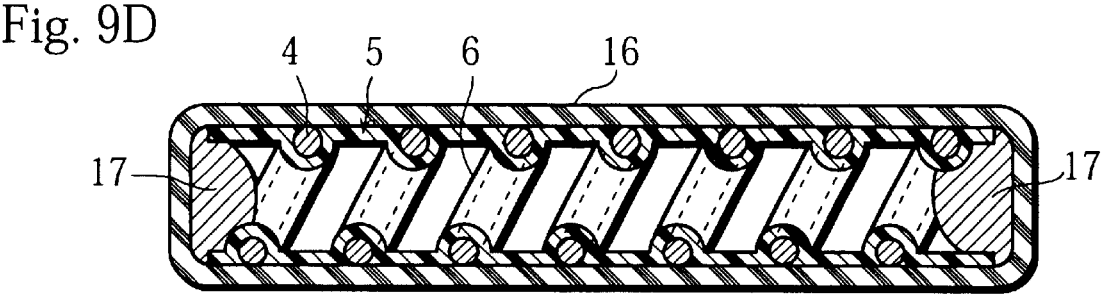
FIG. 9D is an enlarged cross-sectional view showing a fourth process of the manufacturing method relating to the present invention.
Figure 9E:
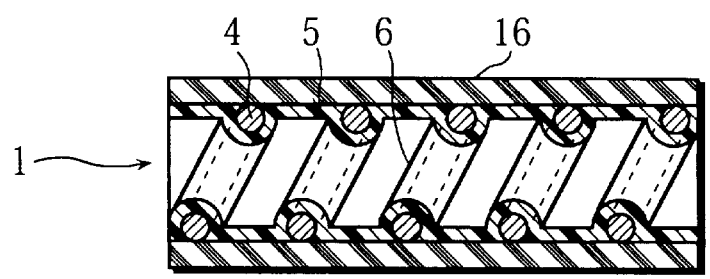
FIG. 9E is an enlarged cross-sectional view showing a fifth process of the manufacturing method and a flexible tube relating to the present invention.

Next, as shown in FIG. 9D and FIG. 9E, a process in which the outer face of the wall 5 is coated with biocompatible material 16 is conducted to obtain the flexible tube 1 for artificial blood vessels of the present invention.

In FIG. 9D, the coating is conducted by dip-coating. Concretely, openings at the both ends of the wall 5 are plugged with sealing material 17, and the plugged wall 5 is dipped in solvent in which the biocompatible material 16 is solved to form the coating layer. As the sealing material 17, epoxy resin, silicone resin, etc. can be used. In FIG. 9E, the end portions of the wall 5 plugged with the sealing material 17 are cut to finish the process.

As the biocompatible material 16 in the present invention, polyurethan, silicone, poly-para-xylylene (parylene), etc. can be used. Among these materials, polyurethan is preferably used because polyurethan is excellent in extendability, strength (anti-fatigue), and blood compatibility (especially, segmented polyurethan is excellent in anti-thrombosis), and dip-coating can be conducted with polyurethan.

And, thickness of the coating layer formed with the biocompatible material 16 is set to be 0 μm to 2000 μm, more preferably 1 μm to 100 μm. If the thickness is less than 1 μm, the strength is decreased, and if the thickness is more than 1000 μm, extendability (elasticity and softness of the artificial blood vessel) is decreased.

In the present invention, as the coating method of the biocompatible material 16 on the outer face of the wall 5, not restricted to specific methods, dip-coating, spray coating, painting, etc. can be used. However, in case that the biocompatible material is resin such as polyurethan, dip-coating is preferable as shown in FIG. 9D because the biocompatible material can be diluted by solvent.

As described above, the flexible tube 1 for artificial blood vessel of the present invention can restrict crimp phenomenon and buckling when the tube 1 is bent even with a small diameter because the coil 4 is embedded in the wall 5. Further, in case that the flexible tube I of the present invention is applied to living organism, endoderm cells are formed smoothly because the spiral convex portion 6 formed on the inner face of the wall 5 of the flexible tube 1 is effective for regeneration of vascular tissue.

And, with the manufacturing method of the present invention, an artificial blood vessel (flexible tube) having a desired outer diameter, especially, artificial blood vessel of small diameter can be easily made because the outer diameter of the wall can be easily controlled by setting the outer diameter of the coil and the inner diameter of the tube appropriately. Further, wall of the artificial blood vessel(in which the wall 5 and the coating layer of the biocompatible material 16 are layered) can be thin and uniform.

Examples of the present invention are shown below concretely. The second embodiment of the present invention is shown in Example 1 and Example 2, and a flexible tube was actually made according to the manufacturing method shown in FIG. 7. And, the third embodiment of the present invention is shown in Example 3, and a flexible tube was actually made according to the manufacturing method shown in FIG. 9.

EXAMPLE 1

First, as shown in FIG. 7A, a coil formed with soft stainless steel (having outer diameter of 1.3 mm, length of 12.2 mm, diameter of the wire of 0.1 mm, pitch of winding of 0.65 mm, and 19 times of winding) is inserted to a silicone tube (of which inner diameter is 1.4 mm, wall thickness is 0.15 mm. and length is 15 mm). Then, as shown in FIG. 7B, surface of the coil and outer and inner faces of the tube are coated with poly-para-xylylene (manufactured by ThreeBond Co., Ltd. under the trade name "parylene") by vapor-deposition as to have thickness T of 5 $\mu$m. The vapor-deposition is conducted with heating temperature of 75° C., heating time of 30 minutes, cracking furnace heating temperature of 680° C, partial pressure of vapored poly-para-xylylene of 0.1 Torr to 0.2 Torr (preferably 0.1 Torr). Finally, as shown in FIG. 7C, the flexible tube is obtained after removing the resin layer coated on the outer face of the tube and the tube. The resin layer is removed by polishing first, and then, the tube is removed by etching.

Dimensions and mechanical characteristics of the obtained flexible tube are measured. Consequently, the outer diameter of the flexible tube is 1.3 mm to 1.4 mm, and the inner diameter is 1.1 mm to 1.09 mm. These values suggest that a flexible tube having unconventionally small diameter and thin wall thickness can be made according to the manufacturing method of the present invention. And, the flexible tube of the present invention having minimum bending radius of about 1 mm is excellent also in mechanical characteristics.

EXAMPLE 2

A flexible tube is made as Example 1 except that the coil formed with soft stainless steel has outer diameter of 0.35 mm, length of 20 mm, diameter of the wire of 0.05 mm, pitch of winding of 0.05 mm, and 400 times of winding, the silicone tube has inner diameter of 0.3 mm, wall thickness of 0.1 mm, and length of 25 mm, the heating temperature is 100° C., and the heating temperature is 30 minutes.

Dimensions and mechanical characteristics of the obtained flexible tube are measured. Consequently, the outer diameter of the flexible tube is 0.35 mm to 0.36 mm, and the inner diameter is 0.29 mm to 0.3 mm. These values suggests that unconventional small diameter and thin wall thickness are achieved and mechanical characteristics is excellent also in the flexible tube of this example.

EXAMPLE 3

First, as shown in FIG. 9A, a coil formed with soft stainless steel (having outer diameter of 1.3 mm, length of 12.2 mm, diameter of the wire of 0.1 mm, and pitch of winding of 0.65 mm) is inserted to a silicone tube (of which inner diameter is 1.4 mm, wall thickness is 0.05 mm, and length is 15 mm). Then, as shown in FIG. 9B, surface of the coil and outer and inner faces of the tube are coated with poly-para-xylylene(manufactured by ThreeBond Co., Ltd. under the trade name "parylene") by vapor-deposition as to have thickness T of 0.5 $\mu$m. The vapor-deposition is conducted with heating temperature of 75° C., heating time of 30 minutes, cracking furnace heating temperature of 680° C., partial pressure of vapored poly-para-xylylene of 0.1 Torr to 0.2 Torr (preferably 0.1 Torr). Finally, as shown in FIG. 9C, the resin layer is removed by polishing and the tube is removed by etching to form the wall of the tube.

Further, as shown in FIG. 9D, openings on the both sides of the wall are plugged with epoxy resin, and coating layer is formed by dip-coating of polyurethane (manufactured by Dow Chemical Japan Limited under a trade name "pellethane"). Concretely, a process in which the wall is dipped in polyurethane dissolved in dimethylformamide (temperature: 40° C., composite ratio:polyurethane of 4 percent by weight to dimethylformamide of 100 percent by weight) for 30 minutes and another process in which the wall is heated and dried are conducted 10 times each in turns to form a coated layer.

Finally, as shown in FIG. 9E, both sides of the tube coated with polyurethane on the outer side are cut to obtain a flexible tube for artificial blood vessel of the present invention.

Dimensions of the obtained flexible tube are measured. Consequently, the outer diameter of the flexible tube is 1.3 mm to 1.4 mm, and the inner diameter is 1.0 mm to 1.1 mm. In bending of the flexible tube, buckling is not observed even with the bending radius of 2.25 mm. And crimp phenomenon is also not observed.

According to the flexible tube of the present invention, for the construction in which the metal coil 4 is coated with the resin 3 having very thin dimension T by vapor-deposition, bend (oscillation) is smoothly conducted, the tube is flexible to bending and having thin wall and high torsional rigidity. And, the tube can be bent with keeping the cross section circular, or compressed in the axis direction. Therefore, the tube having the small outer diameter Do of several millimeters which is impossible to make with conventional flexible tubes, can be realized.

And, sufficiently thin wall is achieved with thin layer of the coated resin 3 because the flexible tube has a construction in which the coil 4 is embedded in the wall 5. Further, uniformity of the thickness of the wall 5 is easily controlled. With this flexible tube, endoscopes, catheters, and guide wires having unconventionally small diameter can be made.

And, sufficiently thin wall is achieved with thin layer of the coated resin 3 because the flexible tube has a construction in which the coil 4 is embedded in the wall 5. Further, uniformity of the thickness of the wall 5 is easily controlled. With this flexible tube, (unconventional) artificial blood vessel, in which crimp phenomenon and buckling in bending are restricted, is realized.

Further, a flexible tube excellent in both of strength (such as torsional rigidity) and flexibility (against bending) can be realized.

According to the manufacturing method for the flexible tube of the present invention, a flexible tube having a small outer diameter $D_0$ of several millimeters and thin wall, which can be smoothly bent, is easily made. Especially, the wall thickness (thickness dimension) T is very thin and the resin layers 3a and 3b are firmly united with the metal coil 4 because the resin layers are formed by vapor-deposition.

And, a flexible tube excel lent in mechanical characteristics, in which crimp phenomenon and buckling in bending are restricted and thin wall thickness and small diameter are achieved, is easily made.

And, a flexible tube excellent in mechanical characteristics, in which crimp phenomenon and buckling in bending are restricted and thin wall thickness and small diameter are achieved, is easily made. Therefore, artificial blood vessel of small diameter is easily made.

And, a uniform thin film is formed on an intricate configuration, the thickness of the thin film is accurately controlled, and the flexible tube is made better thereby.

Further, the tube is excellent in extendability, strength (anti-fatigue ability), and blood compatibility for polyurethane resin (especially, segmented polyurethane is excellent in anti-thrombotic characteristics) as the biocompatible material 16.

While preferred embodiments of the present invention have been described in this specification, it is to be understood that the invention is illustrative and not restrictive, because various changes are possible within the spirit and indispensable features.

What is claimed is:

1. A flexible tube having an inner diameter equal to or less than 5 mm, comprising:
    a metal coil made of a metal wire with a diameter of 0.01 to 0.2 mm;
    a resin film made by vapor-deposition, said resin film coating at least a part of the metal coil and formed into a configuration of a small tube.

2. A flexible tube comprising:
    a coil;
    a wall formed with vapor-deposited resin, the wall comprising a spiral convex portion formed along the coil only on an inner face of the wall,
    wherein the coil is embedded in the spiral convex portion.

3. The flexible tube as set forth in claim 2, wherein an outer diameter of the wall is an outer diameter of the coil+(0 $\mu$m to 50 $\mu$m).

4. A flexible tube comprising:
    a coil;
    a wall formed with vapor-deposited resin comprising a spiral convex portion formed along the coil only on an inner face of the wall; and
    a coating layer formed with a biocompatible material on an outer face of the wall.

5. The flexible tube as set forth in claim 4, wherein an outer diameter of the wall is an outer diameter of the coil+(0 $\mu$m to 50 $\mu$m).

* * * * *